US00PP34252P2

(12) United States Plant Patent
Van Dijk

(10) Patent No.: US PP34,252 P2
(45) Date of Patent: May 17, 2022

(54) ***ANTHURIUM* PLANT NAMED 'AN2608442'**

(50) Latin Name: ***Anthurium andraeanum* L.**
Varietal Denomination: AN2608442

(71) Applicant: ANTHURA B.V., Bleiswijk (NL)

(72) Inventor: Jan Van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,845

(22) Filed: Nov. 23, 2021

(51) Int. Cl.
*A01H 5/02* (2018.01)
*A01H 6/00* (2018.01)

(52) U.S. Cl.
USPC ..... Plt./365
CPC ..... *A01H 6/00* (2018.05)

(58) Field of Classification Search
USPC ..... Plt./365
CPC ..... A01H 6/00; A01H 5/02
See application file for complete search history.

(56) References Cited

PUBLICATIONS

Dummen Orange Tropical Plants Catalog 2020-2021, downloaded from (https://siteadmin.dummenorange.com/site/documents/6209/2021-tropical-plants.pdf) on Dec. 14, 2021, pl 11 and p. 49.*

* cited by examiner

*Primary Examiner* — Anne Marie Grunberg
(74) *Attorney, Agent, or Firm* — Jondle & Associates, P.C.

(57) ABSTRACT

A new *Anthurium* plant named 'AN2608442' particularly distinguished by having weakly blistered and medium glossy, white with pink shade, concave, orbicular-cordate, and durable spathes that retain the original color for a very long period of time, with dark green, narrow ovate, durable leaves, red spadices with dark reddish-orange tips, early and rich flowering continuously throughout the year, and a plant height of 23.0 cm to 28.0 cm is disclosed.

3 Drawing Sheets

Genus and species: *Anthurium andraeanum* L.
Variety denomination: 'AN2608442'.

BACKGROUND OF THE NEW PLANT

The present invention comprises a new and distinct variety of *Anthurium*, botanically known as *Anthurium andraeanum* L., and hereinafter referred to by the variety name 'AN2608442'. The new *Anthurium* plant is a product of a planned breeding program conducted by the inventor in Bleiswijk, the Netherlands. The objective of this breeding program was to create a new plant with a height of 23.0 cm to 28.0 cm having small, weakly blistered and medium glossy, white with pink shade, concave, orbicular-cordate, and durable spathes.

The new variety originated from a cross-pollination made in January 2014 in Bleiswijk, the Netherlands. The female parent was a white *Anthurium* pot plant designated '27814-05' (unpatented), and the male parent was a pink *Anthurium* pot plant designated '27191-010' (unpatented).

A single plant was selected from the progeny of the stated cross in December 2015. Asexual reproduction of the new variety by tissue culture in 2017 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Nov. 26, 2020 (Application no. 2020/2997), by Applicant who obtained the subject matter disclosed directly from the inventor. 'AN2608442' has not been made publicly available or sold anywhere in the world prior to the effective filing date of this application with the exception of sales or disclosures made one year or less before the effective filing date of this claimed invention by Applicant who obtained 'AN2608442' directly from the inventor.

SUMMARY OF THE INVENTION

The following are the most outstanding and distinguishing characteristics of this new variety when grown under normal horticultural practices in Bleiswijk, the Netherlands:

1) Small, weakly blistered and medium glossy, white with pink shade, orbicular-cordate spathes;
2) Red spadices with dark reddish-orange tips;
3) Green, narrow ovate leaves;
4) Spathe shape in lateral view is concave; and
5) Leaf shape in cross-section of middle zone is concave.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 28-week-old plant grown in a greenhouse in Bleiswijk, the Netherlands, in September 2021. Colors in the photographs may differ from the color values cited in the detailed botanical description, which accurately describe the actual colors of the new variety.

DESCRIPTION OF THE NEW VARIETY

Figure 1:
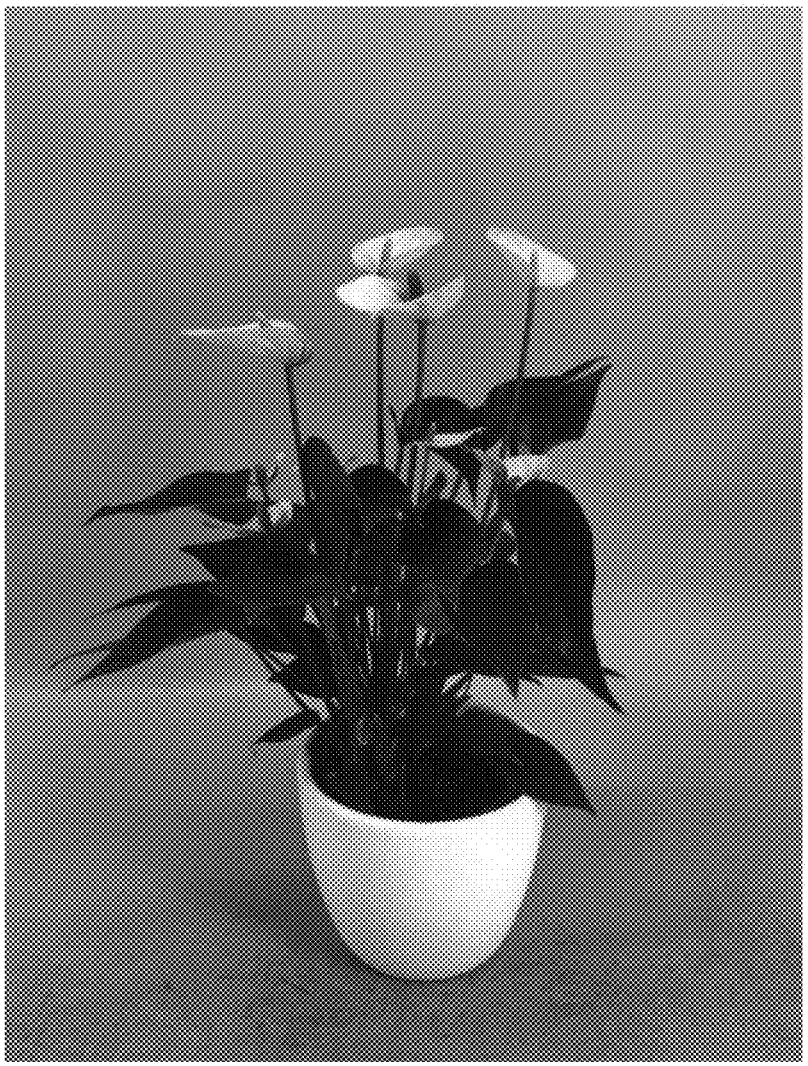
FIG. 1 shows the overall plant habit, including blooms and foliage.
Figure 2:
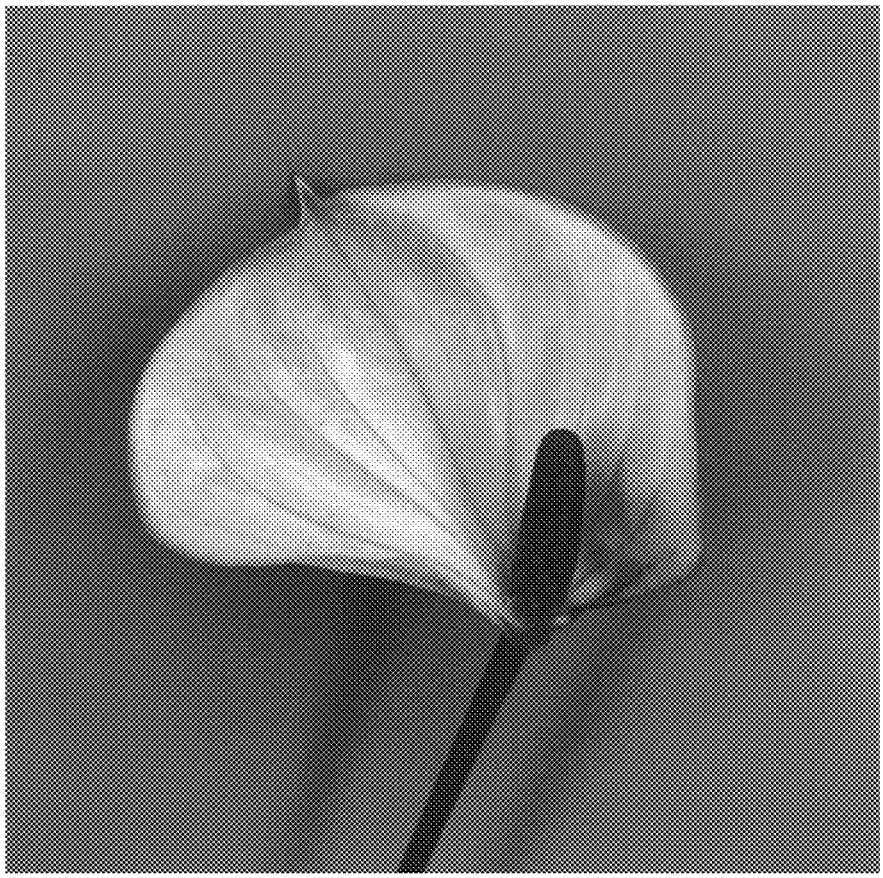
FIG. 2 shows a close-up of the mature spathe.
Figure 3:
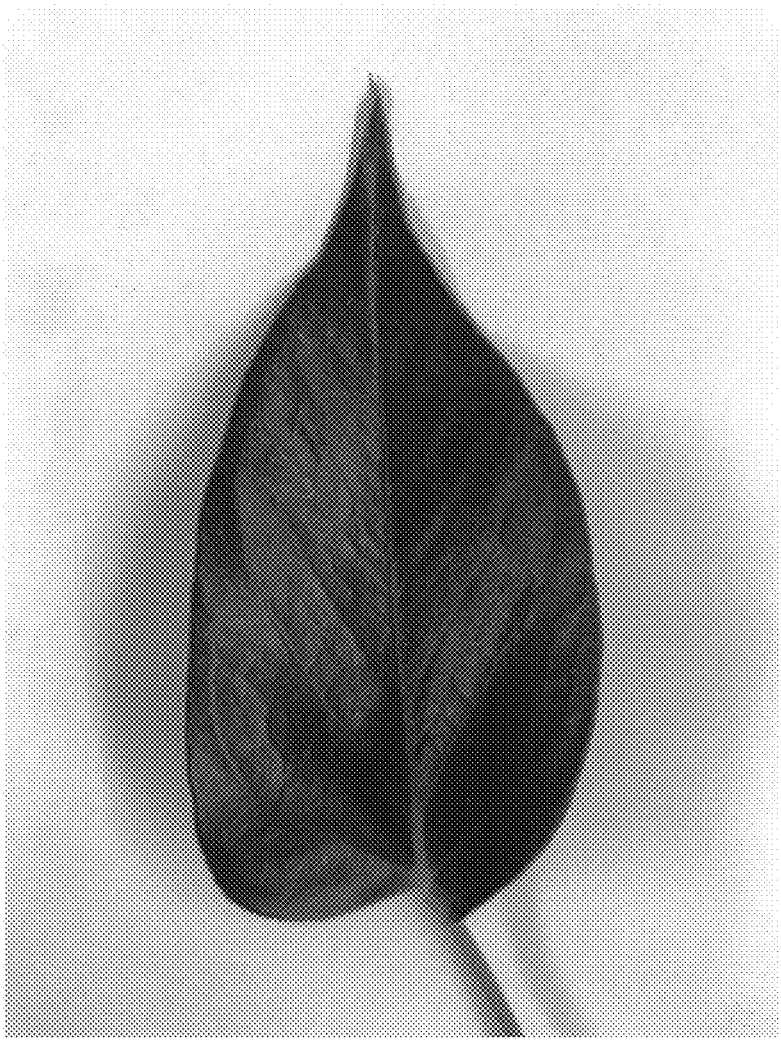
FIG. 3 shows a close-up of the upper leaf blade surface.

The following detailed description sets forth the distinctive characteristics of 'AN2608442'. The data which define these characteristics were collected from asexual reproductions carried out in Bleiswijk, the Netherlands. The plant history was taken on 28-week-old plants which were planted from tissue culture in 9-centimeter (diameter) pots and grown in a glass greenhouse between 19° C. and 24° C. Observations were made in September 2021. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'AN2608442'.

Parentage:

*Female parent*.—*Anthurium* plant '27814-05' (unpatented).

*Male parent*.—*Anthurium* plant '27191-010' (unpatented).

Plant:

*Propagation*.—Tissue culture.

*Root description*.—Fleshy-creamy (RHS 160C) colored roots with small hairy lateral roots having yellow (RHS 9A) colored root tips.

*Time to produce a finished flowering plant*.—28 to 30 weeks after planting in a 9-cm (diameter) pot.

*Growth habit*.—Upright.

*Height* (*measured from soil, including inflorescence*).—23.0 cm to 28.0 cm.

*Width* (*measured from leaf tips*).—24.0 cm to 26.0 cm.

Leaves:

*Immature leaves*.—Length: 7.0 cm to 9.0 cm. Width: 4.5 cm to 5.5 cm. Color: Upper surface: RHS 146A. Lower surface: RHS 146B. Texture (both upper and lower surfaces): Glossy, leathery, and thin.

*Mature leaves*.—Length (fully expanded): 9.0 cm to 11.0 cm. Width: 5.5 cm to 6.5 cm. Shape: Narrow ovate. Apex: Acuminate. Base: Truncate. Leaf blade angle with the petiole: Between 120 degrees and 140 degrees. Leaf margin: Entire. Color: Upper surface: RHS 147A. Lower surface: RHS 146B. Texture: Upper surface: Leathery and thick. Lower surface: Glossy, leathery, and thick. Blistering (upper surface): Very weak. Venation: Pinnate veining; the mid-vein and primary veins (the veins that radiate out from the junction of petiole and leaf) protrude at the underside of the leaf blade. Venation color: Upper surface: RHS 144A. Lower surface: RHS 144B.

*Lobes*.—Absent.

*Petiole*.—Cross-section: Round. Diameter: 0.2 cm to 0.3 cm. Length: 10.0 cm to 13.0 cm for a mature leaf size. Color: Mature leaf: RHS 144A. Immature leaf: RHS 144B. Cataphyll color surrounding the petiole: Outside: RHS 144A. Inside: RHS 144C.

*Geniculum*.—Length: 1.0 cm to 1.5 cm. Width: 0.2 cm to 0.3 cm. Color: RHS 144A.

Inflorescence:

*Arrangement*.—Single.

*Flowering habit* (*length of flowering season*).—Continuous.

*Number of inflorescences per plant*.—7 to 9.

*Fragrance*.—Absent.

*Longevity of inflorescence on plant*.—Over a year.

Spathe:

*Buds*.—The spathe is tightly rolled around the spadix and extrudes from the peduncle sheath. After the spathe is fully opened the peduncle elongates some extra centimeters.

*Arrangement*.—Spathe angle with the peduncle is between 90 degrees and 110 degrees; the spathe stands on a wiry peduncle about 3.0 cm to 6.0 cm above the foliage.

*Shape*.—Orbicular cordate.

*Apex*.—Mucronate.

*Base*.—Cordate.

*Texture*.—Weakly blistered and medium glossy.

*Margin*.—Weakly undulated.

*Size*.—Length: 4.5 cm to 5.5 cm. Width: 4.5 cm to 5.5 cm.

*Lobes*.—Present. Arrangement: The spathe has two lobes extending past the peduncle. The lobes are non-touching. Length: 0.2 cm to 0.3 cm. Width: 1.0 cm to 2.0 cm.

*Color*.—Just fully open: Upper surface: White (RHS 155B) with a pink shade (RHS 56A) and touch of pink (RHS 51A) at the base, margin, and toward the tip. Lower surface: White (RHS 155C) with a pink shade (RHS 56B) toward the tip. This color remains for a very long period, at least more than 30 weeks after opening. The spathe turns green after some weeks.

Peduncle:

*Shape*.—Erect.

*Cross-section*.—Round.

*Length*.—18.0 cm to 20.0 cm.

*Diameter*.—0.2 cm to 0.3 cm.

*Color*.—RHS 144A.

Flowering time:

*General*.—One small, rooted, untreated tissue culture plant of 8.0 cm tall will flower, depending on the season, after 28 to 30 weeks and 7 to 8 blossoms appear. More blossoms appear after some additional weeks so that a full flowering and commercial plant will have 8 to 9 spathes. Smaller blossoms may occur on immature plants.

Spadix:

*Size*.—Length: 1.5 cm to 2.5 cm (depending on flower size). Width (at apex): 0.3 cm to 0.4 cm. Width (at base): 0.4 cm to 0.5 cm.

*Shape*.—Columnar.

*Angle of spadix tip with peduncle*.—140 degrees to 160 degrees.

*Texture*.—When the spathe is unfurling, the spadix is smooth. When the spadix matures, small stigmata protrude. The stigmata are evenly distributed around the spadix. The spadix matures from base to top, slowly giving the spadix a somewhat rough appearance.

*Color*.—Immature: RHS 178B. Mature: RHS 183D. Ages to: RHS 146B.

Flowers:

*Quantity per spadix*.—70 to 100.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 182D.

Reproductive organs:

*Stamens*.—Not visible.

*Pollen amount*.—Absent.

*Pistil*.—Quantity: 70 to 100. Length: Less than 0.01 cm. Color: RHS 182D.

*Style*.—Not observed to date.

*Stigma*.—Shape: Ovoid. Diameter: Less than 0.01 cm. Color: RHS 182D.

*Ovary*.—Rarely visible.

*Ovary color*.—Not measured.

Fruit and seed set: None observed to date.

Disease and pest resistance: No specific resistance or susceptibility observed to pathogens or pests common to *Anthurium* under commercial conditions to date.

COMPARISON WITH PARENTAL AND SIMILAR COMMERCIAL VARIETIES

'AN2608442' differs from the female parent plant '27814-05' (unpatented) in that 'AN2608442' has white spathes with pink shade and red spadices with dark reddish-orange tips, whereas '27814-05' has white spathes and white spadices with green tips.

'AN2608442' differs from the male parent plant '27191-010' (unpatented) in that 'AN2608442' has white spathes with pink shade and red spadices with dark reddish-orange tips, whereas '27191-010' has pink spathes and purplish-red spadices with dark purplish-red tips. Additionally, 'AN2608442' has narrower spadices than '27191-010'.

'AN2608442' differs from similar commercial variety 'ANTHYQDAL' (U.S. Plant Pat. No. 31,334) in that 'AN2608442' has orbicular-cordate spathes and narrow ovate leaves, whereas 'ANTHYQDAL' has cordate spathes and ovate-cordate leaves. Additionally, 'AN2608442' has narrower spathes than 'ANTHYQDAL'.

'AN2608442' differs from similar variety 'ANTHDOSDOH' (U.S. Plant Pat. No. 27,887) in that 'AN2608442' has orbicular-cordate, white spathes with pink shade and narrow ovate leaves, whereas 'ANTHDOSDOH' has lanceolate, pink spathes and lanceolate leaves. Additionally, 'AN2608442' has wider spathes than 'ANTHDOSDOH'.

I claim:

1. A new and distinct variety of *Anthurium* plant named 'AN2608442', substantially as illustrated and described herein.

* * * * *